United States Patent [19]

Franco et al.

[11] Patent Number: 4,988,677
[45] Date of Patent: Jan. 29, 1991

[54] MACROLIDE ANTIBIOTIC AND ITS USE AS A MEDICINAL AGENT

[75] Inventors: Christopher M. M. Franco; Julia Gandhi; Sugata Chatterjee; Goukanapalli C. S. Reddy; Bimal N. Ganguli; Richard H. Rupp, all of Bombay, India; Herbert Kogler, Kelkheim; Hans-Wolfram Fehlhaber, Idstein/Taunus, both of Fed. Rep. of Germany

[73] Assignee: Hoechst Aktiengesellschaft, Frankfurt am Main, Fed. Rep. of Germany

[21] Appl. No.: 89,238

[22] Filed: Aug. 25, 1987

[30] Foreign Application Priority Data

Aug. 27, 1986 [DE] Fed. Rep. of Germany ....... 3629063

[51] Int. Cl.$^5$ ...................... A61K 31/71; C07H 17/08
[52] U.S. Cl. ...................................... 514/30; 536/7.1
[58] Field of Search .......................... 536/7.1; 514/30

[56] References Cited

U.S. PATENT DOCUMENTS 4,794,173 12/1988 Umezana et al. ................... 536/7.1
4,835,141 5/1989 Cullen et al. ........................ 536/7.1

OTHER PUBLICATIONS

H. Achenbach and W. Karl, J. of Antibiotics: vol. 29 (4):76-22 (Apr. 1976).
Kenji Kinoshita, Shuzo Satoi, Mitsuo Hayashi, J. of Antibiotics: vol. 38 (4):522-526 (Apr. 1985).
Sugata Chatterjee, et al., J. of Antibiotics: vol. 51 (10):1368-1374 (Oct. 1987).

*Primary Examiner*—Johnnie R. Brown
*Assistant Examiner*—Elli Peselev
*Attorney, Agent, or Firm*—Finnegan, Henderson, Farabow, Garrett, and Dunner

[57] ABSTRACT

The present invention relates to the macrolide antibiotic swalpamycin, to a microbiological process for its preparation, to a new microorganism strain Streptomyces species, and to the use of swalpamycin as a medicinal agent for the treatment of infections caused by bacteria, mycoplasmas and Actinomycetes.

4 Claims, 5 Drawing Sheets

MACROLIDE ANTIBIOTIC AND ITS USE AS A MEDICINAL AGENT

The present invention relates to the macrolide antibiotic swalpamycin, to a microbiological process for its preparation using the microorganism strain Streptomyces species Y-84,30967 (DSM 3740), and to its use as a medicinal agent and animal feed additive.

The Streptomyces species culture number HIL Y-84,30967, called Str. sp. Y-84,30967 hereinafter, was isolated from a sample of soil collected at Pune, Maharashtra (India). Variants and mutants of this strain can be obtained in a known manner using a mutagen such as N-methyl-N-nitro- N'-nitrosoguanidine or by ultraviolet light. The microorganism Str. sp. Y-84,30967 belongs to the order Actinomycetales, the family Streptomycetaceae and the genus Streptomyces. It is known of known of some Streptomyces species that they produce antibiotics of the macrolide type, and the latter have been described in the literature (T. Osono, Y. Oka, S. Watanabe, Y. Numazaki, K. Moriyama, H. Ishida, K. Suzuke, Y. Okami and H. Umezawa; J. Antibiotics 20, 174 (1967); S. Omura, Y. Hironaki and T. Hata: J. Antibiotics 23, 511 (1970); I. Haupt, H. Fricke, J. Cerna and I. Rychlik: J. Antibiotics 29, 1314 (1976); S. Omura and H. Tanaka in "Macrolide Antibiotics, pp. 3–35, S. Omura (Editor), Academic Press, Orlando, Fla., USA (1984).

Str. sp. Y-84,30967 is regarded as a new strain because it differs in some of its morphological, cultural and physiological properties from the known strains, as is evident from the description which follows. Another reason for this is that it produces a new macrolide antibiotic, called swalpamycin herein, and a new macrolide aglycone, called swalpanolide, as indicated in the description which follows.

Macrolide antibiotics are of importance in medicine as antimicrobial agents against a wide spectrum of Gram-positive bacteria and mycoplasmas. To date, various macrolide antibiotics have been described, for example erythromycin, leukomycin, oleandomycin, spiramycin and midecamycin, which are used clinically, and tylosin which is used in veterinary practice.

Macrolides are described in a number of review articles (Z. Vankek and J. Majer in "Antibiotics", volume 2, pages 154–188; D. Gottlieb and P. D. Shaw (Editors), Springer, New York (1967); D. Vasquez in "Antibiotics", volume 3, pages 459–479; J. W. Corcoran and F. E. Hahn (Editors), Springer, New York; J. Berdy in "CRC Handbook of Antibiotic Compounds", volume 2, pages 39–156, CRC Press, Boca Raton, Fla. (1980)).

Furthermore, a compilation of macrolide antibiotics is to be found in "Index of Antibiotics from Actinomycetes", Hamao Umezawa (Chief Editor), volume I, pages 114, 123, 135, 171, 172, 207, 223, 275, 373, 382–384, 604–606, 640–641 and 669, Univ. Park Press, State College, Pa., USA; (1967), and volume II, pages 254, 255, 287–289, 305, 357–362, 481, 483, 508, 509, 532–537, 549–550, 573–579, 630–635, 639–641, 809–823 and 1013–1014, Univ. Park Press, Baltimore, USA (1978).

The book "Macrolide Antibiotics—Chemistry, Biology and Practice" edited by S. Omura and published by Academic Press, Orlando, Fla., USA (1984) contains a comprehensive review of the macrolide antibiotics, their biosynthesis, chemical derivatization, chemical synthesis and importance in clinical and veterinary practice.

The macrolide antibiotics are divided into 3 main groups according to the size of the macrocylic lactone ring which forms the aglycone (A. K. Mallams in "Macrolides", page 156, M. Grayson (Editor), Wiley, New York (1982)). The first group is formed by the group of 12-membered macrolides comprising methymycin, neomethymycin and YC-17. The second group is composed of the 14-membered macrolides, and its important members are erythromycin, oleandomycin, lankamycin, kujimycin, megalomicin, picromycin and narbomycin. The third group comprises the 16-membered macrolides which can be subdivided into (a) the basic macrolide antibiotics which contain at least one aminosugar residue, this subgroup embracing a large number of antibiotics which include, as representatives and scientifically important compounds, angolamycin, leukomycins, spiramycins, maridomycins, carbomycins, cirramycins, rosamycin, macinamycins, M-4365 $G_1$ and $G_2$, and tylosin;

(b) the neutral macrolide antibiotics which contain no aminosugar.

Members of this subgroup to be mentioned are chalcomycin (P. W. K. Woo et al., J. Amer. Chem. Soc. 84, 880; 1512; 1066 (1962)), neutramycin (D. V. Lefemine et al., Antimicrob. Agents Chemother., page 41 (1961)), aldagamycins (M. P. Kunstmann et al., Antimicrob. Agents Chemother., page 87 (1964)) and some mycinamycins (K. Kinoshita et al., J. Antibiotics, 38, 522–526 (1985)). As is evident from the detailed description of the invention which follows, the swalpamycin according to the invention belongs to this neutral macrolide subgroup, but differs from chalcomycin, neutramycin and the aldgamycins and mycinamycins, as can be seen from the HPLC chromatogram (see FIG. 1) and the physicochemical and spectroscopic properties (see FIGS. 2–5).

Hence the present invention relates to the macrolide antibiotic swalpamycin of the formula I and to the macrolide aglycone swalpanolide of the formula II This invention further relates to a process for the preparation of the macrolide antibiotic swalpamycin of the formula I, and of the macrolide aglycone swalpanolide of the formula II and of chalcomycin. The process comprises culturing Str. sp. Y-84,30967 (DSM 3740) under aerobic conditions, at a temperature between 18° and 37° C., in an aqueous nutrient medium which contains sources of assimilable carbon and nitrogen, together with essential mineral salts at a pH between 6 and 9, until the medium exhibits a substantial antibiotic activity, and obtaining the fermentation product from the medium.

The new antibiotic according to the invention is active against a number of pathogenic microorganisms, including Gram-positive bacteria and mycoplasmas, and accordingly can be used in human and veterinary medicine. In particular, swalpamycin is suitable as a therapeutic medicinal agent for the treatment of infectious diseases caused by Gram-positive bacteria and mycoplasmas, for example *Staphylococcus aureus, Streptococcus pyogenes, Diplococcus pneumoniae, Legionella pneumoniae*, Rickettsia strains, Spirochaeta, Toxoplasma, *Clostridium tetani, Bacteroides fragilis, Mycobacterium kansasi, Mycoplasma gallinarum, Mycoplasma pneumoniae, Chlamydia trachomatis* etc., The new antibiotic according to the invention is furthermore active against strains which are resistant to various antibiotics including erythromycin. It can also be used as an animal feed additive. Swalpamycin can be used in every bioavailable form either alone or combined with chalcomycin.

The strain Streptomyces sp. Y-84,30967 is obtained from a sample of soil by culturing at a pH of 6.5 to 8.5 in a nutrient medium which is composed of sources of carbon and nitrogen, inorganic nutrient salts and solidifying agents. Suitable sources of carbon are glucose, starch, dextrin, glycerol, sucrose and molasses. The suitable sources of nitrogen are peptone, yeast extract, beef extract, malt extract and casein. Agar is a possible example of a solidifying agent. Inorganic nutrient salts include salts of sodium, potassium, magnesium, calcium, phosphorus and sulfur.

The microorganism according to the invention extends colorless aerial mycelia from branched substrate mycelia. Spore chains are formed in spirals over the aerial mycelia. Neither whorls or asci are observed. The cultural properties of the microorganism on various agar media can be described as follows:

| 1. Yeast extract/malt extract agar | |
|---|---|
| growth | copious |
| aerial mycelium | copious, white to pinkish gray, powdery |
| underside | pale brown |
| soluble pigment | negative |
| 2. Oatmeal agar | |
| growth | copious |
| aerial mycelium | copious, white to gray to pale brown, powdery |
| underside | pale yellow |
| soluble pigment | negative |
| 3. Inorganic salts/starch agar | |
| growth | copious |
| aerial mycelium | copious, gray to brownish gray, powdery |
| underside | pale brown |
| soluble pigment | negative |
| 4. Glycerol/asparagine agar | |
| growth | good |
| aerial mycelium | weak, white, powdery |
| underside | pale yellow |
| soluble pigment | negative |
| 5. Peptone/yeast extract/iron agar | |
| growth | moderate |
| aerial mycelium | negative |
| underside | dark brown to black |
| soluble pigment | brownish black |
| 6. Tyrosine agar | |
| growth | good |
| aerial mycelium | good, white to pinkish gray, powdery |
| underside | brownish black |
| soluble pigment | pale brown |
| 7. Sucrose/nitrate agar | |
| growth | weak |
| aerial mycelium | sparse, white, powdery |
| underside | pale brown |
| soluble pigment | negative |
| 8. Glucose/asparagine agar | |
| growth | moderate |
| aerial mycelium | weak, white to grayish brown, powdery |
| underside | pale yellow |
| soluble pigment | negative |
| 9. Nutrient agar | |
| growth | moderate |
| aerial mycelium | negative |
| underside | pale brown |
| soluble pigment | negative |

The optimal temperature range for growth of the microorganism according to the invention is 25° C. to 35° C. The microorganism liquefies gelatin in a glucose/peptone/gelatin medium, hydrolyzes starch in a starch/inorganic salt agar, and causes skim milk to coagulate.

The formation of a melanoid pigment is observed in tyrosine agar, peptone/yeast extract/iron agar and tryptone/yeast extract broth.

The pattern of assimilation of this microorganism for sources of carbon is as follows (in Pridham-Gottlieb medium):

Positive: D-glucose, L-arabinose, D-xylose, i-inositol, D-mannitol, D-fructose, raffinose, galactose, maltose, cellobiose, Na glutamate, mannose, lactose.

Weakly positive: sucrose

Negative: ramnose, cellulose, salicin, dulcitol.

With regard to the formation of the known 16-membered neutral macrolide antibiotics such as chalcomycin, nutramycin, the aldgamycins, mycinamycins and bandamycins, the following known microorganisms may be compared with Str. sp. Y-84,30967: *Streptomyces bikiniensis, Streptomyces albogriseolus, Streptomyces rimosus, Streptomyces goshikiensis* and *Streptomyces lavendulae.*

As is known, mycinamycins are formed by *Micromonospora griseorubida* sp. nov.

The published data on the cultural and physiological properties of these known microorganisms exhibit distinct differences between the microorganism according to the invention and the abovementioned known microorganisms. For example, Streptomyces Lavendulae and Streptomyces goshikiensis belong to the red series, and Streptomyces rimosus belong to the white series, whereas the microorganism according to the invention is to be included in the gray series. Streptomyces albogriseolus can be differentiated from Streptomyces sp. Y-84,30967 on the basis of the formation of melanoid pigment. The microorganism according to the invention exhibits distinct differences from Streptomyces bikiniensis in the pattern of assimilation of sources of carbon. Furthermore, on fermentation the microorganism according to the invention forms chalcomycin and a new macrolide antibiotic of the formula I, which is called swalpamycin and contains a new 16-membered macrolide aglycone. On the basis of the abovementioned observations it is concluded that the microorganism according to the invention represents a new species of Streptomyces. The microorganism strain was deposited at the Deutsche Sammlung von Mikroorganismen (German Microorganism Collection, D-3400 Göttiongen) on May 20, 1986, under receipt number DSM 3740.

It is obvious to the expert that this invention is not confined to the specific microorganism defined above but includes all those mutants which are derived, spontaneously and artificially, from the said microorganism and which are able to form the new antibiotic swalpamycin and the new macrolide aglycone swalpanolide.

The process for the preparation of the compounds which belong to the class of macrolide antibiotics comprises culturing Str. sp. Y-84,30967 (DSM 3740) at a pH between 6.0 and 7.0 and a temperature between 20° and 40° C., under aerobic conditions, in a nutrient medium containing sources of carbon and nitrogen, inorganic nutrient salts and trace elements, and obtaining the compounds from the culture broths and the mycelium in a known manner which is described hereinafter.

Suitable sources of carbon for the nutrient medium for the preparation of the new antibiotics are glucose, starch, dextrin, glycerol, sucrose, molasses and oil, suitable sources of nitrogen are soybean meal, yeast extract, beef extract, malt extract, cornsteep liquor, peptones and casein, and suitable inorganic nutrient salts are sodium chloride, magnesium sulfate, ammonium sulfate and calcium carbonate. Iron, manganese, copper, zinc and cobalt can be used as trace elements.

Str. sp. Y-84,30967 (DSM 3740) is preferably cultivated at 25°–30° C., particularly preferably at 27° C., and pH 6.5. The fermentation is terminated after 40–45 hours, when the highest yields of the compounds are obtained. The fermentation is preferably carried out as submerged fermentation. The progress of the fermentation and the formation of the antibiotic macrolide compounds can be followed by the antibacterial activity of the culture liquid and the mycelium against Staphylococcus aureus 209 P.

Swalpamycin can be obtained from the filtrate at pH 6.0–7.5, preferably pH 6.5, as a mixture with chalcomycin by use of conventional methods, such as extraction with solvents which are immiscible with water, such as chloroform, methylene chloride, n-butanol, ethyl acetate or butyl acetate, with ethyl acetate being preferred as the solvent which is immiscible with water.

The antibiotic complex can be obtained from the mycelium or the entire culture broth by extraction of the mycelium cake with an organic solvent, for example a ketone, preferably acetone. This entails the acetone extract being concentrated, the aqueous layer being adjusted to pH 6.0–7.5, preferably pH 6.5, and being extracted with organic solvents which are immiscible with water, such as chloroform, methylene chloride, n-butanol, ethyl acetate or butyl acetate, with ethyl acetate being preferred as solvent. The ethyl acetate extracts of the mycelium and of the culture filtrate can be combined or worked up separately.

Another method for obtaining swalpamycin from the culture broth is based on adsorption. For ths purpose the liquid substance, for example the culture filtrate or the solvent extract containing the compound according to the invention, is subjected to column chromatography or liquid chromatography etc., using suitable adsorbents such as active charcoal, ®Diaion HP-20, ®XAD 4, alumina, silica gel or ®Sephadex LH-20. The compound according to the invention is eluted from the adsorbents using suitable mobile phases such as chloroform, methanol or acetone, alone or in combination with one another or with water, and the eluates are evaporated to dryness.

A variety of methods can be used for obtaining and purifying the compounds according to the invention from the abovementioned solvent extracts or concentrated eluate containing swalpamycin and chalcomycin. For example, for the isolation and purification, it is possible and expedient to combine adsorption and elution processes with active charcoal, ®Amberlite. ®XAD-4 and 7 (Röhm and Haas Co.) or ®Diaion HP-20 (Mitsubishi Chemical Industries), gel filtration with ®Sephadex LH-20 (Pharmacia Fine Chemicals AB) and equivalent products, and adsorption chromatography on alumina and silica gel, etc. Also suitable are thin-layer chromatography, medium pressure and high-performance liquid chromatography using suitable adsorbents such as silica gel and silanized silica gel C18 with suitable solvent systems. Furthermore, the said purpose can be met by countercurrent chromatography with a defined solvent system.

Swalpamycin is a colorless amorphous powder which is soluble in methanol, ethanol, n-propanol, isopropanol, n-butanol, ethyl acetate, n-butyl acetate, acetone, ethyl methyl ketone, methyl isobutyl ketone, methylene chloride, chloroform, dimethylformamide and dimethyl sulfoxide. Swalpamycin is sparingly soluble or insoluble in hexane, petroleum ether (40°–60°) and water.

In the thin-layer chromatography systems (TLC) detailed below, swalpamycin and chalcomycin show the following results:

| TLC plate: silica gel precoated plate (Article No. 5554 from E. Merck, Darmstadt) | | | |
|---|---|---|---|
| Rf | in MeOH:CHCl$_3$ (7:93) | MeOH:CHCl$_3$ (1:9) | Ethyl acetate |
| Swalpamycin | 0.5 | 0.6 | 0.7 |
| Chalcomycin | 0.42 | 0.53 | 0.46 |

Figure 1:
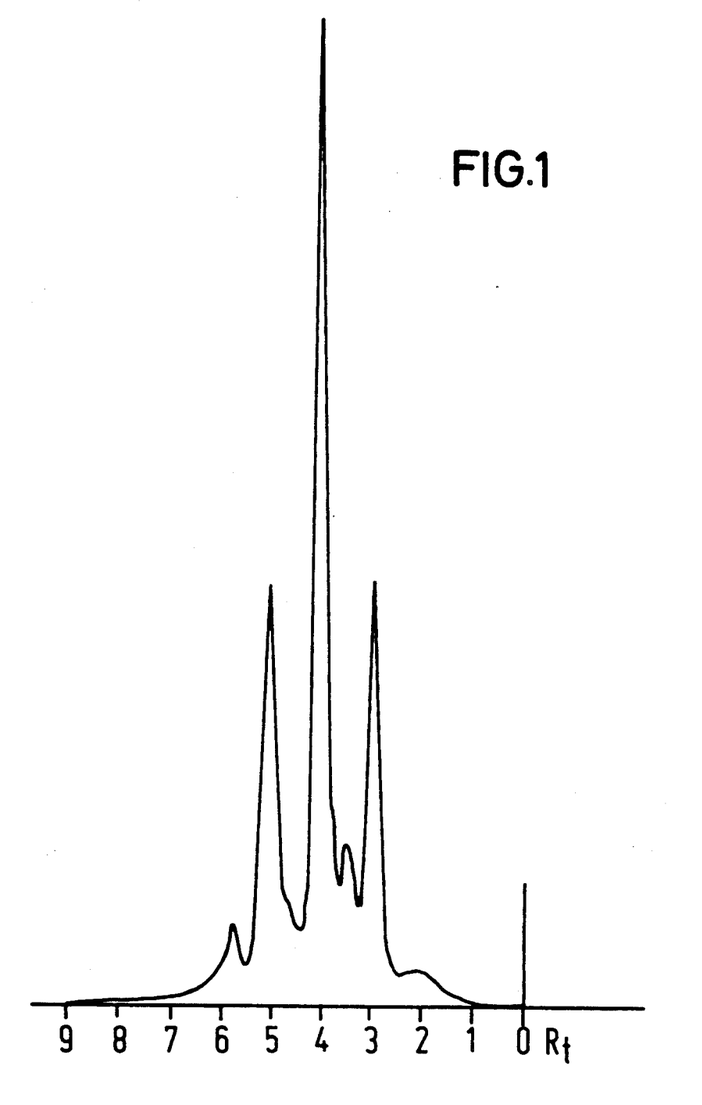
Figure 2:
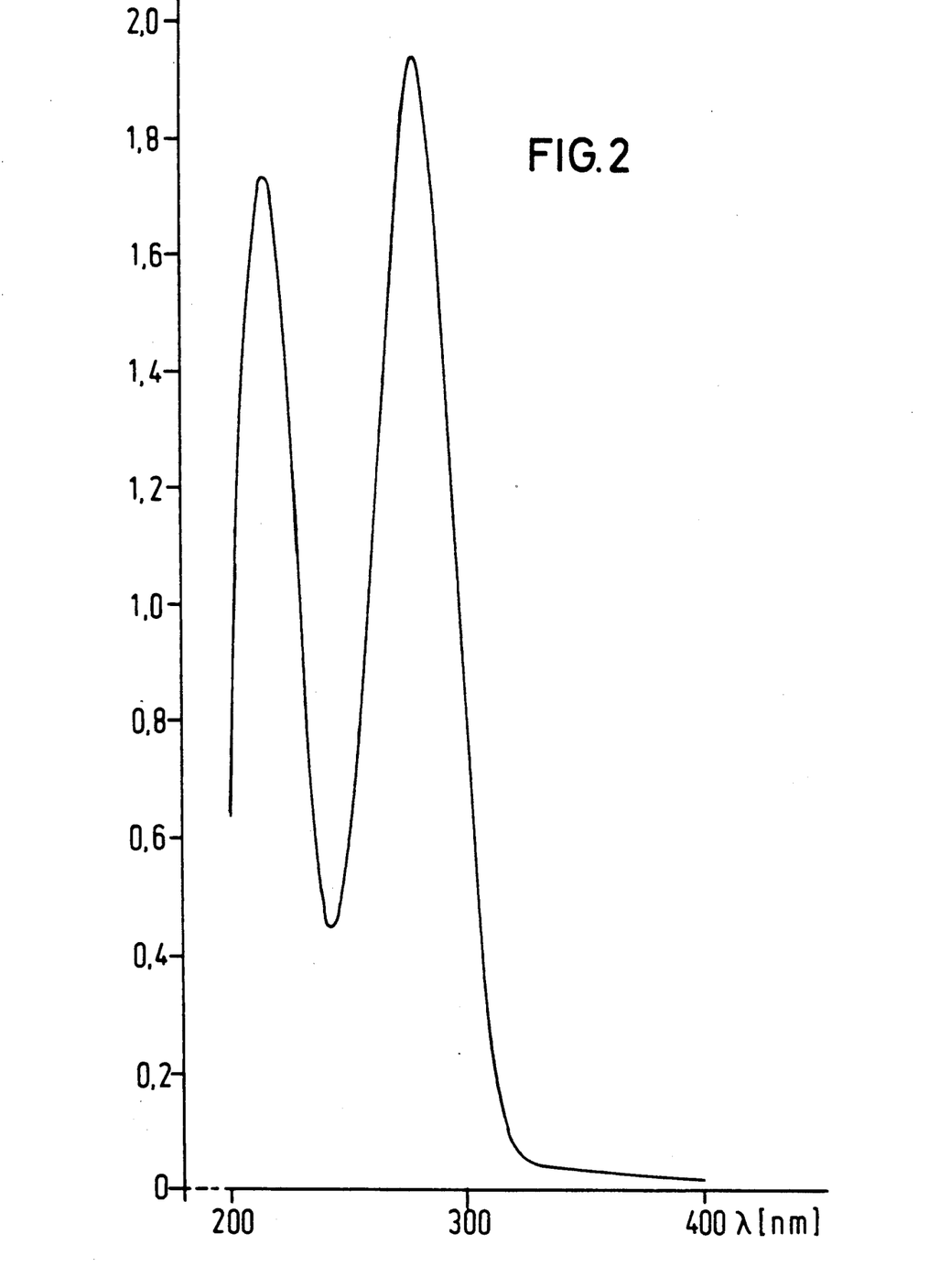
Figure 3:
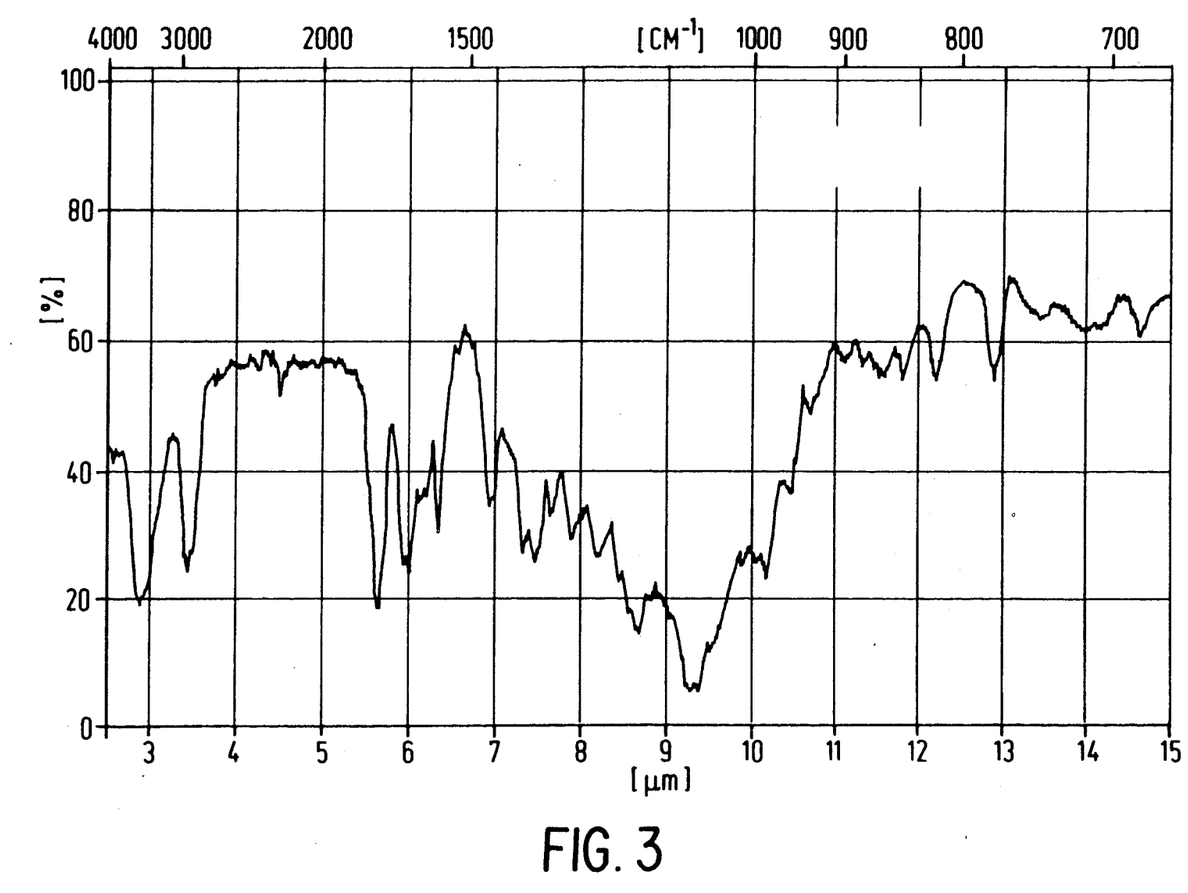

The retention times of swalpamycin and chalcomycin in the analytical high-performance liquid chromatography (HPLC) shown in FIG. 1 are:

| | |
|---|---|
| column packing | ®Lichrosorb RP18 |
| flow rate | 1 ml/min |
| detection | at 216 nm |

| solvent | MeOH:H₂O (7:3) |
| --- | --- |
| Retention time | |
| Swalpamycin | 5.7 min |
| Chalcomycin | 5.0 min |

Swalpamycin melts at 126°–129° C. and has an optical rotation of $[\alpha]_d^{20} = -3.8°$ (c=0.21 in CHCl₃).

Spectroscopic data for swalpamycin are as detailed below:

1. UV $\lambda_{max}$ in methanol: see appended FIG. 2. A solution with a concentration of 0.2 g/l swalpamycin was used to determine the UV absorption maxima. The absorption spectrum was measured in the range 200 to 800 nm.
2. The IR spectrum (KBr disk) was determined using a Perkin Elmer P.E.521 IR spectrometer—see appended FIG. 3.

The ¹H and ¹³C nuclear magnetic resonance spectra were determined at 90 MHz and 22.5 MHz, respectively, in CDCl₃ using a Jeol Fx-90 Fourier transform nuclear magnetic resonance spectrometer, with Me₄Si as internal standard.

Figure 4:
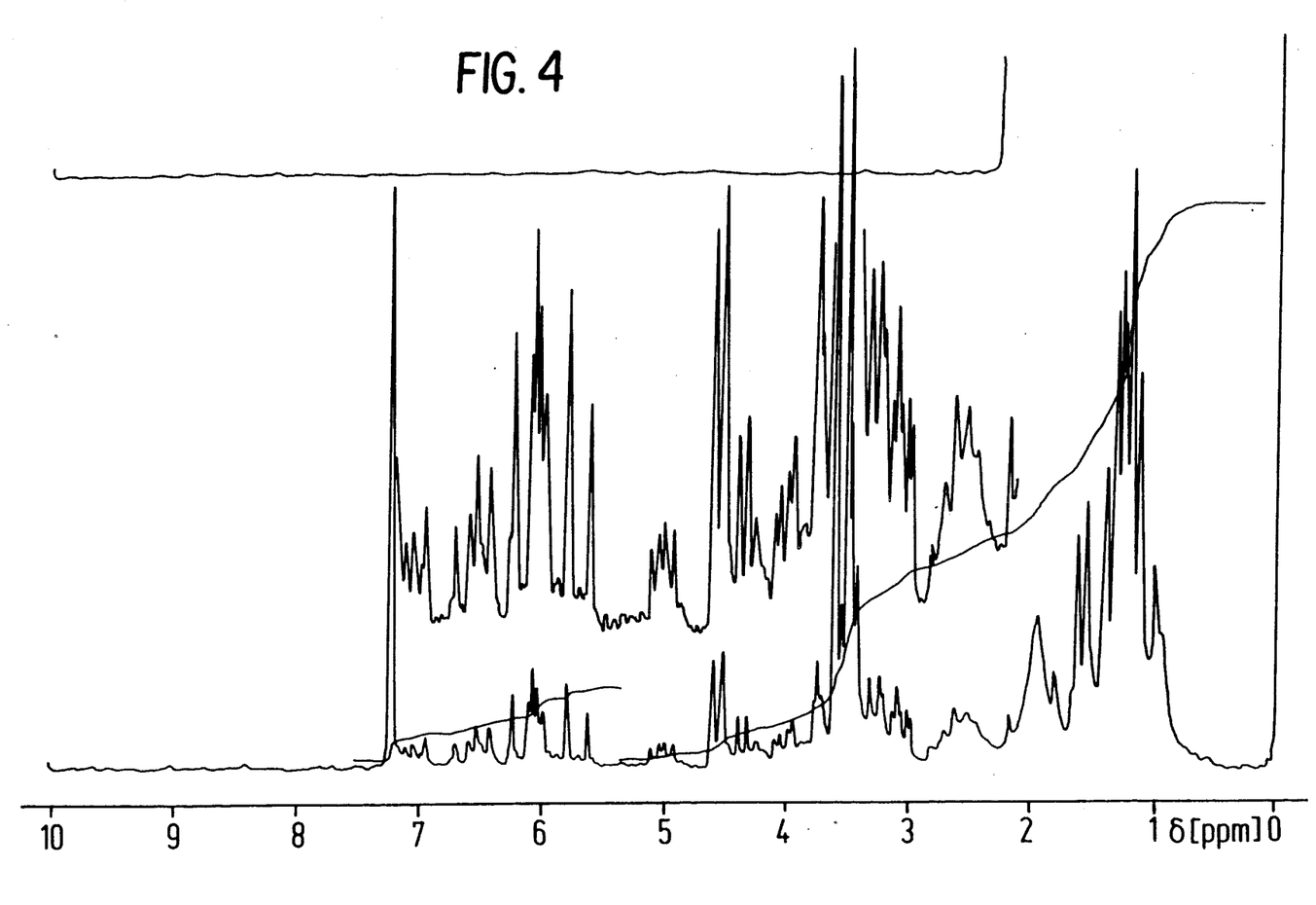
Figure 5:
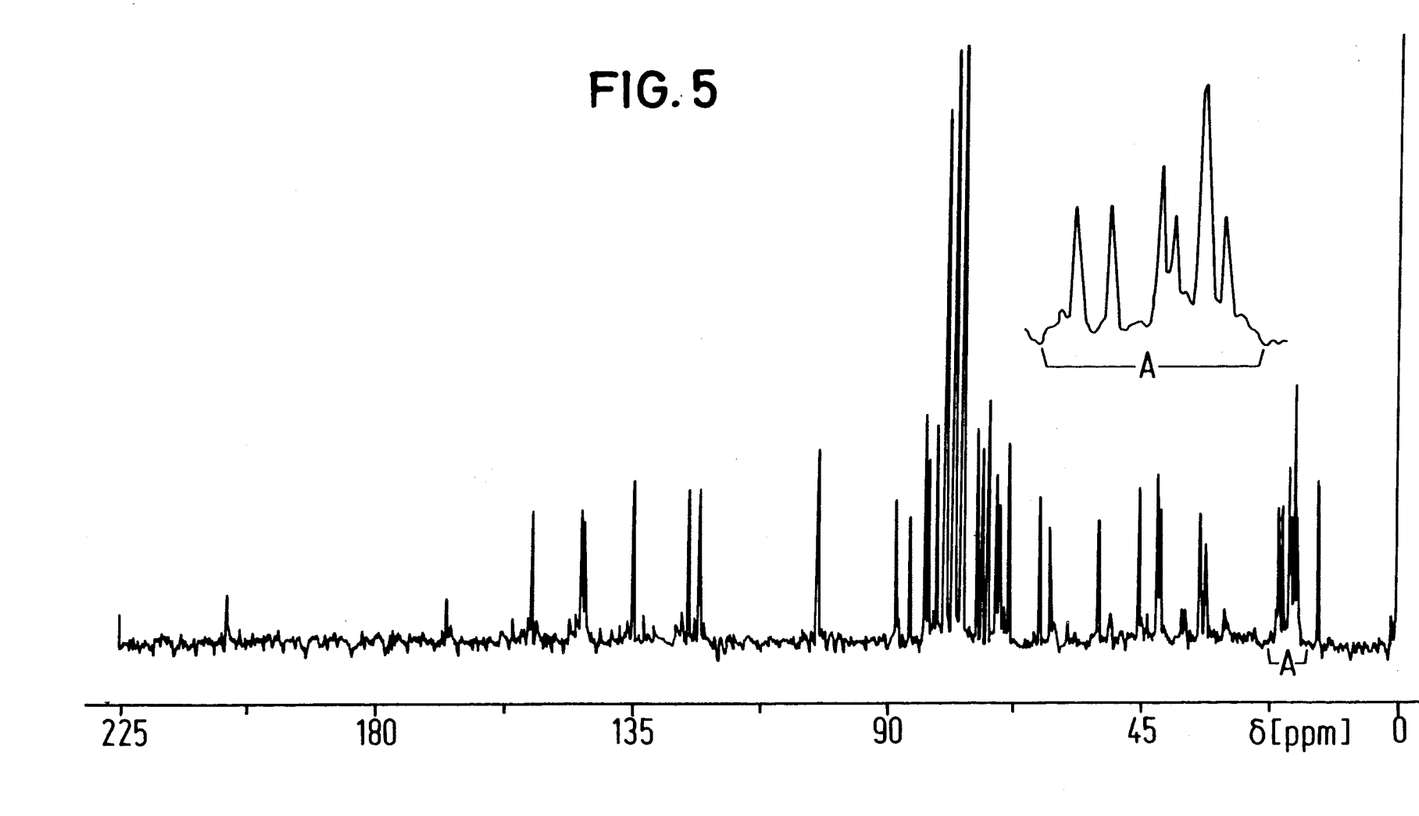

3. ¹H NMR spectrum—see appended FIG. 4.
4. ¹³C NMR spectrum—see appended FIG. 5.
5. The mass-spectrographic investigations were carried out on the silylated derivative of swalpamycin by electron impact ionization, and the atomic formula for each peak, including the M⁺ peak, was determined by high-resolution mass measurements.

The molecular weight and empirical formula resulting from this were as follows:

| Swalpamycin | molecular weight: | 724 |
| --- | --- | --- |
| | empirical formula: | $C_{37}H_{56}O_{14}$. |

From the available data, which are described above, it is concluded that the structures of swalpamycin and swalpanolide are those shown above in formulae I and II, respectively.

In laboratory agar plate tests, swalpamycin exhibits an antimicrobial spectrum against bacteria, mycoplasmas and Actinomycetes. It acts in vitro against sensitive and resistant strains of *Staphylococcus aureus* and *Streptococcus faecalis*, as well as strains of *Bacillus subtilis*, *Sarcina lutea*, *Streptococcus pyogenes*, *Micrococcus luteus*, *Mycoplasma gallinarum* and *Mycoplasma pulmonis*. The minimum inhibitory concentration (MIC) of swalpamycin has been determined for various microorganisms. The results are to be found in Table I which follows:

TABLE I

| | | MIC of swalpamycin |
| --- | --- | --- |
| No. | Test organism | Swalpamycin |
| 1. | S. aureus 209P | 6.3 |
| 2. | S. aureus 20424 Mac$^R$ | 50 |
| 3. | S. aureus 3066 Meth.$^R$ | 3.2 |
| 4. | S. aureus R 85.Em$^R$ | 12.5 |
| 5. | S. aureus R85/M, Em$^R$ | >50 |
| 6. | S. aureus 712 Meth$^R$ | 12.5 |
| 7. | S. aureus 789 Meth.$^R$ | >50 |
| 8. | Strept. faecalis UD 86 | >50 |
| 9. | Strept. faecalis Eder:Mac$^R$ | >50 |
| 10. | Micrococcus luteus | 1.6 |
| 11. | Sarcina lutea | 0.2 |
| 12. | Bacillus subtilis | 0.1 |
| 13. | S. aureus MLS 11.Em$^R$ | 25 |
| 14. | S. aureus MLS 14.Em$^R$ | 25 |
| 15. | S. aureus MLS 16.Em$^R$ | 12.5 |

TABLE I-continued

| | | MIC of swalpamycin |
| --- | --- | --- |
| No. | Test organism | Swalpamycin |
| 16. | Candida albicans | >50 |
| 17. | E. coli 9632 | >50 |
| 18. | E. coli ESS 2231 | >50 |
| 19. | Ps. aeruginosa M 35 | >50 |
| 20. | Pr. vulgaris | >50 |
| 21. | Ent. cloacae | >50 |
| 22. | Prov. stuartii | >50 |
| 23. | Cit. freundii | >50 |

*Mac = macrolide, Em = erythromycin, Meth = methicillin

Swalpamycin is thus active against Gram-positive bacteria, including erythromycin-resistant strains, and mycoplasma, and can be used for the treatment of infections caused by the above pathogenic bacteria.

Thus the invention also relates to medicinal products, for the treatment of microbial infections, which contain the compound of the formula I.

The compound according to the invention can also be used in combination with other active substances, for example from the series of penicillins, cephalosporins or aminoglycosides.

The compound of the formula I and its physiologically tolerated acid addition salts can be administered orally, intramuscularly or intravenously. Medicinal products which contain swalpamycin as active substance can be prepared by mixing the compound of the formula I with one or more pharmacologically tolerated vehicles or diluents such as, for example, fillers, emulsifiers, lubricants, masking flavors, colorants or buffer substances, and converted into a suitable pharmaceutical form such as, for example, tablets, coated tablets, capsules, or a suspension or solution suitable for parenteral administration.

Examples of vehicles or diluents which may be mentioned are tragacanth, lactose, talc, agar-agar, polyglycols, ethanol and water. Suitable and preferred for parenteral administration are suspensions or solutions in water. It is also possible to administer the active substances as such, without vehicles or diluents, in a suitable form, for example in capsules.

Suitable doses of the compound of the formula I or its physiologically tolerated acid addition salts are about 0.4 to 20 g/day, preferably 0.5 to 4 g/day, for an adult of body weight about 60 kg.

It is possible to administer single doses or, in general, multiple doses, it being possible for the single dose to contain the active substance in an amount of about 50 to 1000 mg, preferably of about 100 to 500 mg.

The examples which follow illustrate the invention:

EXAMPLE 1

Isolation of Streptomyces sp. Y-84,30967 from soil (a) Preparation of the Isolation Nutrient Media

| Medium 1: | |
| --- | --- |
| Glucose | 1.0 g |
| Glycerol | 1.0 g |
| L-Arginine | 0.3 g |
| K₂HPO₄ | 0.3 g |
| MgSO₄.7H₂O | 0.2 g |
| NaCl | 0.3 g |
| Yeast extract | 2.0 g |
| Fe₂(SO₄)₃ | 10 mg |
| CuSO₄.5H₂O | 1 mg |
| ZnSO₄.7H₂O | 1 mg |
| MnSO₄.7H₂O | 1 mg |

-continued

| | |
|---|---|
| Agar | 15.0 g |
| Distilled water | 1 liter |
| pH | 6.5 |
| Medium 2: | |
| Glucose | 2.0 g |
| L-Asparagine | 1.0 g |
| K$_2$HPO$_4$ | 0.5 g |
| MgSO$_4$.7H$_2$O | 0.5 g |
| Soil extract | 200 ml |
| Agar | 15.0 g |
| Distilled water | 800 ml |
| pH | 8.0 |
| Medium 3: | |
| Starch | 10.0 g |
| Casein | 0.3 g |
| KNO$_3$ | 2.0 g |
| NaCl | 2.0 g |
| K$_2$HPO$_4$ | 2.0 g |
| MgSO$_4$.7H$_2$O | 0.05 g |
| CaCO$_3$ | 0.02 g |
| FeSO$_4$ | 0.01 g |
| Agar | 15.0 g |
| Distilled water | 1 liter |
| pH | 7.2-7.5 |

The media were sterilized at 121° C. for ½ hour.

(b) Preparation of the Soil Suspension

A gram of soil is suspended in distilled water, shaking vigorously. The soil is allowed to settle out, and the supernatant liquid is used to inoculate each of the abovementioned isolation media.

(c) Inoculation of the Isolation Medium

Petri dishes containing 50 ml of one of the abovementioned isolation nutrient media are each inoculated with 1 ml of soil suspension.

(d) Isolation of Streptomyces sp. Y-84,30967

The inoculated Petri dish is incubated at 30° C. for two weeks and Streptomyces sp. Y-84,30967 is isolated from the growing microorganisms.

EXAMPLE 2

Culturing of Streptomyces sp. Y-84,30967 for the Preparation of Swalpamycin by Fermentation Streptomyces sp. Y-84,30967 is maintained on yeast-malt agar of the following composition:

| | |
|---|---|
| Malt extract | 10.0 g |
| Yeast extract | 4.0 g |
| Glucose | 4.0 g |
| Agar | 15.0 g |
| Distilled water | 1 liter |
| pH | 7.0 |

The medium is distributed over test tubes and sterilized at 121° C. for 30 minutes. To prepare agar slants, the tubes are cooled in an inclined position. Each agar slant is inoculated with the culture and incuibated at 28° C. for 10-15 days, by which time good growth and spore formation is observed. A distilled water suspension of spores from an agar slant is used to inoculate 5×500 ml Erlenmeyer flasks each containing 100 ml of seed culture medium or one 5 l aspirated bottle containing 1 L of the same seed culture medium.

Composition of the seed culture medium

| | |
|---|---|
| Glucose | 15.0 g |
| Soybean meal | 15.0 g |
| Cornsteep liquor | 5.0 g |
| CaCO$_3$ | 2.0 g |
| NaCl | 5.0 g |
| Distilled water | 1 liter |
| pH | 6.5 |

The above medium is distributed in 100 ml portions over 500 ml Erlenmeyer flasks or in 1 L portions in 5 l aspirator bottles and sterilized for 30 minutes at 121° C. The flasks/bottles are cooled, inoculated with the spore suspension and shaken at 27° C. (±1° C.) on a rotary shaker with a 38 mm throw at 240 rpm for 72 hours. The product which has grown is used to inoculate two 15 l glass fermentation vessels, each containing 10 l of 8-10% by volume seed culture medium, for the preparation of the second seed culture stage. The fermentation is carried out at 27° C. (±1° C.), stirring at 180-200 rpm and aerating at 6-7 liters/min, for a period of 24 hours. The resulting, well-grown second seed culture stage is used for inoculation of the production medium.

Composition of the production medium

| | |
|---|---|
| Glucose | 15.0 g |
| Soluble starch | 20.0 g |
| Soybean meal | 3.0 g |
| Peptone | 3.0 g |
| CaCO$_3$ | 2.0 g |
| NaCl | 2.0 g |
| Cornsteep liquor | 2.0 g |
| (NH$_4$)$_2$SO$_4$ | 0.5 g |
| Distilled water | 1 liter |
| pH | 6.5 |

0.025% Desmophen ® is added to the contents of the fermentation vessel as antifoam agent.

280 l of the above medium is placed in a 390 l fermentation vessel and sterilized by indirect and direct steam at 121° C. for 28 minutes. The fermentation vessel is cooled and inoculated with the second seed culture stage (7% by volume). The fermentation is carried out at 27° C. ±1° C.), stirring at 100-200 rpm, for a period of 40-45 hours. The aeration rate is 170 liters per minute. When the fermentation is terminated after 40-45 hours, the diameter of the zone of inhibition of *Staphylococcus aureus* 209P is 16 mm when the culture filtrate is tested by the agar well method (6 mm diameter), with the pH of the culture liquid being in the range 6.4 to 6.8.

The packed cell volume is 28-30%.

The harvested culture broth which contains the antibiotic complex is centrifuged to remove the mycelium, and the culture liquid is further processed as described in Example 6.

EXAMPLE 3

Cultivation of Streptomyces sp. Y-84,30967 for the Preparation of Swalpamycin by Fermentation The process is that of Example 2, with the following differences:

Composition of the agar medium

| | |
|---|---|
| Starch (soluble) | 10.0 g |
| K$_2$HPO$_4$ | 1.0 g |
| MgSO$_4$.7H$_2$O | 1.0 g |
| NaCl | 1.0 g |
| (NH$_4$)$_2$SO$_4$ | 2.0 g |

-continued

| | |
|---|---|
| CaCO₃ | 2.0 g |
| FeSO₄.7H₂O | 0.1 mg |
| MnCl₂.4H₂O | 0.1 mg |
| ZnSO₄.7H₂O | 0.1 mg |
| Agar | 15.0 g |
| Distilled water | 1 liter |
| pH | 7.2 |

Composition of the production medium

| | |
|---|---|
| Glucose | 20.0 g |
| Soybean meal | 10.0 g |
| CaCO₃ | 0.2 g |
| CoCl₂.6H₂O | 0.1 g |
| Distilled water | 1 liter |
| pH | 7.0 |

100 L of the above medium are introduced into a 150 l fermentation vessel and sterilized by direct and indirect steam at 121° C. for 28 minutes. The fermentation vessel is cooled and inoculated with the second seed culture stage (9% by volume). The fermentation is carried out at 27° C. ($\pm 1°$ C, ), stirring at 80–90 rpm, with an aerati rate of 60–70 liters per minute. When the fermentation is terminated after 40–43 hours, the pH of the culture broth is 6.45 and the diameter of the zone of inhibition of Staphylococcus aureus 209P is 15 mm when the culture filtrate is tested by the agar well method (6 mm diameter). The packed cell volume is 18–24%. The culture broth is processed as in Example 7.

EXAMPLE 4

Cultivation of Streptomyces sp. Y-84,30967 for the Preparation of Swalpamycin

The process is that of Example 2, with the following differences:
Composition of the agar medium

| | |
|---|---|
| Oatmeal | 20.0 g |
| Agar | 15.0 g |
| FeSO₄.7H₂O | 0.1 g |
| ZnSO.7H₂O | 0.1 mg |
| MnCl₂.4H₂O | 0.1 mg |
| Distilled water | 1 liter |
| pH | 7.2 |

Composition of the seed culture medium

| | |
|---|---|
| Starch | 30.0 g |
| Sucrose | 10.0 g |
| Glucose | 10.0 g |
| Soybean peptone | 15.0 g |
| Cornsteep liquor | 10.0 g |
| K₂HPO₄ | 3.0 g |
| NaCl | 1.0 g |
| CaCO₃ | 3.0 mg |
| CuSO₄.5H₂O | 7.0 mg |
| FeSO₄.7H₂O | 1.0 mg |
| MnCl₂.4H₂O | 8.0 mg |
| ZnSO₄.7H₂O | 2.0 mg |
| Distilled water | 1 liter |
| pH | 7.2 |

Composition of the production medium

| | |
|---|---|
| Dextrin | 20.0 g |
| Soybean meal | 10.0 g |
| Yeast extract | 2.0 g |

-continued

| | |
|---|---|
| FeSO₄.7H₂O | 0.1 g |
| Distilled water | 1 liter |
| pH | 6.5 |

When the fermentation vessel is harvested after 49 hours the pH of the culture broth is 6.75 and the packed cell volume is 22%. The diameter of the zone of inhibition of Staphylococcus aureus 109P is 15 mm when the culture filtrate is tested by the agar well method (6 mm).

The harvested culture broth is further processed as in Example 6.

EXAMPLE 5

Cultivation of Streptomyces sp. Y-84,30967 for the Preparation of Swalpamycin by Fermentation The process is that of Example 3, with the following differences:
Composition of the production medium

| | |
|---|---|
| Peptone | 10.0 g |
| Beef extract | 5.0 g |
| Glucose | 20.0 g |
| NaCl | 5.0 g |
| CaCO₃ | 3.0 g |
| Distilled water | 1 liter |
| pH | 6.5 |

When the fermentation vessel is harvested after 46 hours, the pH of the culture broth is 6.5 and the packed cell volume is 27%, and the culture filtrate has an activity of 16 mm (diameter of the zone of inhibition) when tested by the agar well method (6 mm diameter).

The harvested culture broth is further processed as in Example 7.

EXAMPLE 6

Isolation and Purification of Swalpamycin

The fermentation broth obtained in Example 2 is centrifuged to separate the mycelium and culture filtrate. The culture filtrate (232 l) obtained in this way is, if necessary, adjusted to pH 6.5 with 2N HCl, and is extracted twice with 120 l of ethyl acetate each time. The aqueous layers are discarded, and the combined ethyl acetate extracts are evaporated to dryness in vacuo. The amount of crude extract which is obtained in this way is 165 g. The mycelium (14.5 kg) is extracted twice with 45 l of acetone each time. The combined extracts are evaporated in vacuo to remove the acetone. The aqueous layer thus obtained is adjusted to pH 6.5 with 2N NaOH, 20 l of water are added, and the mixture is extracted three times with 20 l of ethyl acetate each time. The aqueous layers are discarded, and the combined extracts are evaporated to dryness in vacuo. This results in about 110 g of crude extract. The crude extracts from the culture filtrate and the mycelium are combined (275 g), dissolved in 1 l of 10% strength aqueous methanol, and the solution is then treated four times with 1 l of heptane each time. The heptane layer is discarded, and the aqueous layer is concentrated under reduced pressure. After removal of the methanol, the aqueous layer is extracted twice with 500 ml of chloroform each time. The resulting chloroform extract is concentrated under reduced pressure, which provides 110 g of the compound containing the antibiotic mixture.

These 110 g are applied twice in succession to a column containing 3.5 kg of silica gel (mesh size 300–400) and eluted with a solvent system comprising chloroform: methanol (97:3). 6 g of active fraction A and 80 g of active fraction B are obtained in this way. Fraction B is further purified by repeated silica gel chromatography (2.4 kg of silica gel, mesh size 100–200) to give 9 g of semipure chalcomycin and further active fractions.

1 g of semipure chalcomycin is purified by preparative thin-layer chromatography (0.5 mm thick silica gel plates) to give 70 mg of pure chalcomycin. The chalcomycin is identified by its physicochemical properties and spectroscopic analysis. For further purification, fraction A is applied to a column containing 600 g of silica gel RP18, and eluted with a solvent system comprising methanol: water (7:3), with 85 mg of semipure swalpamycin being obtained. It is further purified by preparative thinlayer chromatography (0.5 mm thick silica gel plates) in a mixture of chloroform and methanol (90:10) followed by preparative high-performance liquid chromatography on a ®µ-Bondapak C18 column (Waters) with methanol:water (7:3) as eluent, at a flow rate of 1 ml/minute and using a UV detector at 280 nm. This results in 23 mg of pure swalpamycin.

The swalpamycin is identified by chemical analysis and spectroscopic methods.

EXAMPLE 7

Isolation and Purification of Swalpamycin

About 62 liters of the fermentation broth obtained as in Example 3 are centrifuged to separate the mycelium and culture filtrate. The filtrate from the broth is extracted twice with 30 liters of ethyl acetate each time. The ethyl acetate extracts are combined and evaporated to dryness in a rotary evaporator, which provides 12 g of crude extract. The mycelium is extracted twice with 6 liters of acetone each time. The acetone extracts are combined and, after removal of the acetone, the resulting aqueous layer is extracted with 10 liters of ethyl acetate. The ethyl acetate layer is evaporated to dryness, which provides 8 g of crude extract. The dried crude extracts (20 g) from the culture filtrate and the mycelium are combined and purified by repeated column chromatography on silica gel (mesh size 100–200) using an eluent composed of chloroform with increasing proportions of methanol, namely up to 10% methanol. This method results in 2 g of bioactive fractions. These 2 g of bioactive mixture are triturated with petroleum ether (40–60°), which provides 1.5 g of inactive oily residue and 360 mg of bioactive precipitate. This precipitate is dissolved in a small volume of methanol and passed through a ®Sephadex LH-20 column (70×3.5 cm), with the fractions each being eluted with methanol. This results in approximately 260 mg of semipure antibiotic mixture being obtained, and this is further purified by thinlayer chromatography (0.5 mm thick silica gel plate) in a solvent system composed of 10% methanol in chloroform. 150 mg of chalcomycin, which was identified by chromatography, spectral analysis and its physicochemical properties, 10 mg of bioactive material, and 12 mg of swalpamycin are obtained in this way.

The swalpamycin is identified by chemical analysis and spectroscopic methods.

We claim:

1. A compound of the formula I

2. A pharmaceutical composition comprising 50 to 1,000 mg of the compound as defined in claim 1 in association with a pharmaceutically acceptable carrier.

3. A method of treating infections caused by bacteria, mycoplasma or actinomycetes in a mammal by administering to a mammal an effective amount of the compound as defined in claim 1.

4. A pharmaceutical composition comprising 100 to 500 mg. of the compound as defined in claim 1 in association with a pharmaceutically acceptable carrier.

* * * * *